US00PP37253P2

(12) United States Plant Patent
Arotzarena et al.

(10) Patent No.: US PP37,253 P2
(45) Date of Patent: Feb. 10, 2026

(54) RASPBERRY PLANT NAMED 'Aine'

(50) Latin Name: *Rubus idaeus L*
Varietal Denomination: Aine

(71) Applicant: AROFA S.L., Tajonar (ES)

(72) Inventors: Domingo Arotzarena, Tajonar (ES); Antonio Soto, Tajonar (ES); Francisco Roman, Tajonar (ES)

(73) Assignee: Arofa, S.L., Tajonar (ES)

( * ) Notice: Subject to any disclaimer, the term of this patent is extended or adjusted under 35 U.S.C. 154(b) by 0 days.

(21) Appl. No.: 19/064,491

(22) Filed: Feb. 26, 2025

(51) Int. Cl.
*A01H 5/08* (2018.01)
*A01H 6/74* (2018.01)

(52) U.S. Cl.
USPC ..... Plt./204
CPC ..... *A01H 6/7499* (2018.05); *A01H 5/08* (2013.01)

(58) Field of Classification Search
USPC ..... Plt./204
See application file for complete search history.

*Primary Examiner* — Shubo Zhou
*Assistant Examiner* — Zachariah Allan Kay
(74) *Attorney, Agent, or Firm* — Weatherly IP Solutions, LLC; Karen P. Bechtold; James Weatherly

(57) ABSTRACT

A new raspberry plant named 'Aine' particularly distinguished by large fruit for use in fresh market, primocane variety with two crops per season and very productive plant, and sweet flavor, is disclosed.

3 Drawing Sheets

Genus and species: *Rubus idaeus L.*
Variety denominations: 'Aine'.

BACKGROUND OF THE NEW PLANT 'AINE'

The present invention comprises a new and distinct variety of Raspberry, botanically known as *Rubus idaeus* L, and hereinafter referred to by the variety name 'Aine'. 'Aine' originated from seed of a fruit from female parent '21-03FR-000' (not patented) and an unknown male plant. The seed was found in September 2020 in Applicant's fruit sorting and processing facility in Tariquejo, Villanueva de los Castillejos, Huelva, Spain.

In September 2020, seed from the fruit found at Applicant's facility was planted. 'Aine' was first vegetatively propagated by vegetative cuttings in January 2021 in Tariquejo, Villanueva de los Castillejos, Huelva, Spain.

SUMMARY OF 'AINE'

The following are the most outstanding and distinguishing characteristics of 'Aine' when grown under normal horticultural practices in Tariquejo, Huelva, Spain.

1. Large fruit for use in fresh market;
2. Primocane variety with two crops per season and a very productive plant.
3. Sweet flavor.

DESCRIPTION OF THE PHOTOGRAPHS

This new raspberry plant is illustrated by the accompanying photographs from the 2022-2023 growing season of plants grown in Tariquejo, Villanueva de los Castillejos, Huelva, Spain. The plants are six months old and grown in a hydroponic system. The colors shown are as true as can be reasonably obtained by conventional photographic procedures.

DESCRIPTION OF 'AINE'

Figure 1:
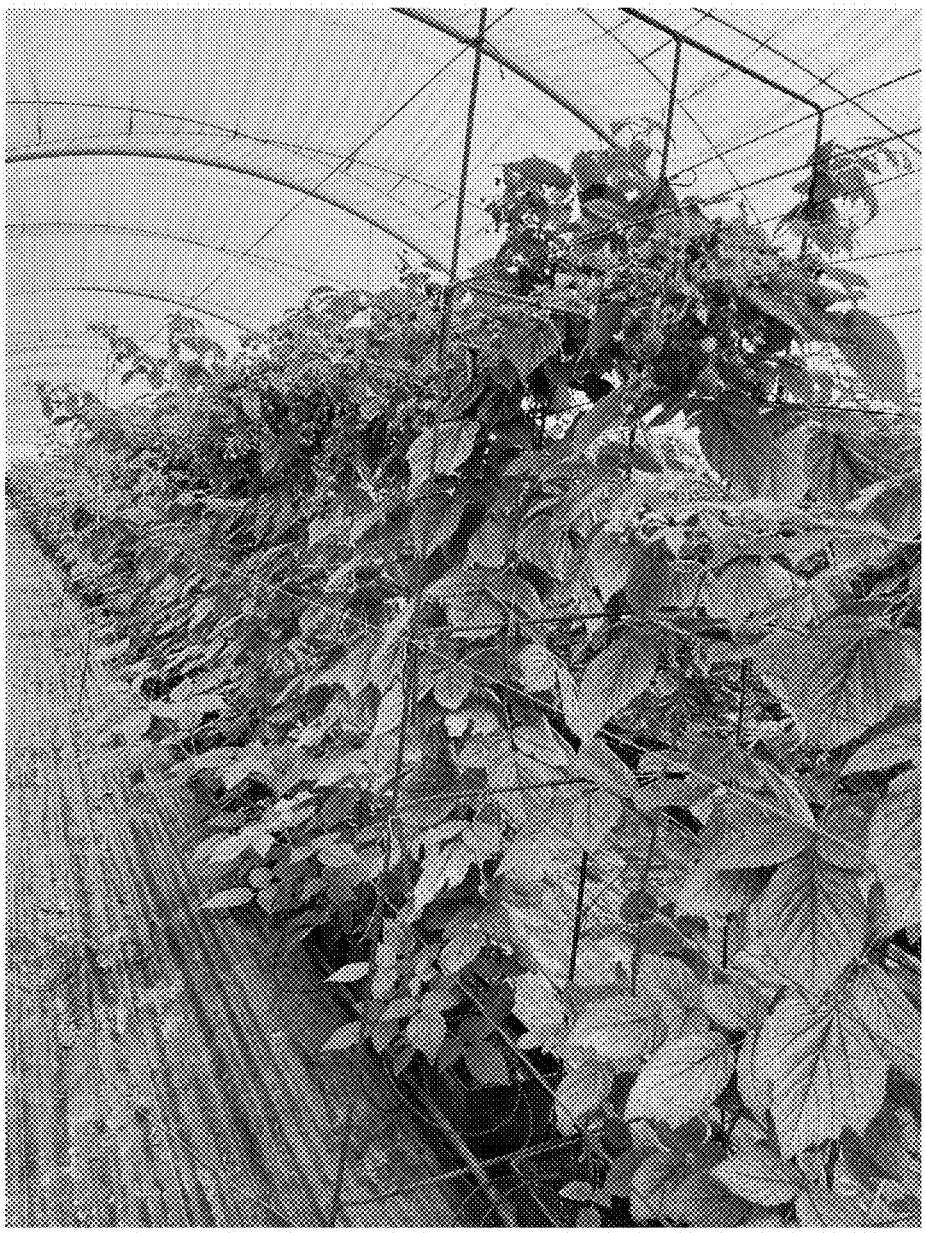
FIG. 1 shows a whole plant of 'Aine' showing foliage, buds, fruit and flowers.
Figure 2:
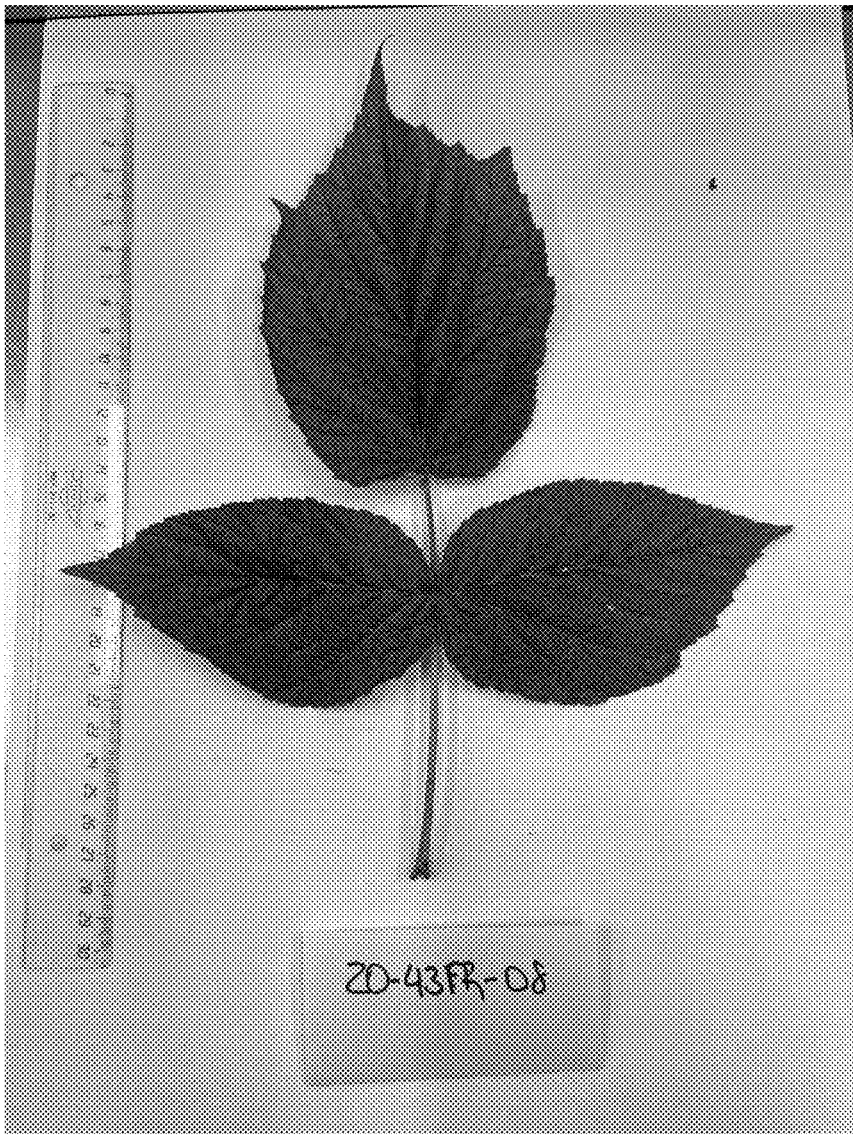
FIG. 2 shows the leaves of 'Aine'.
Figure 3:
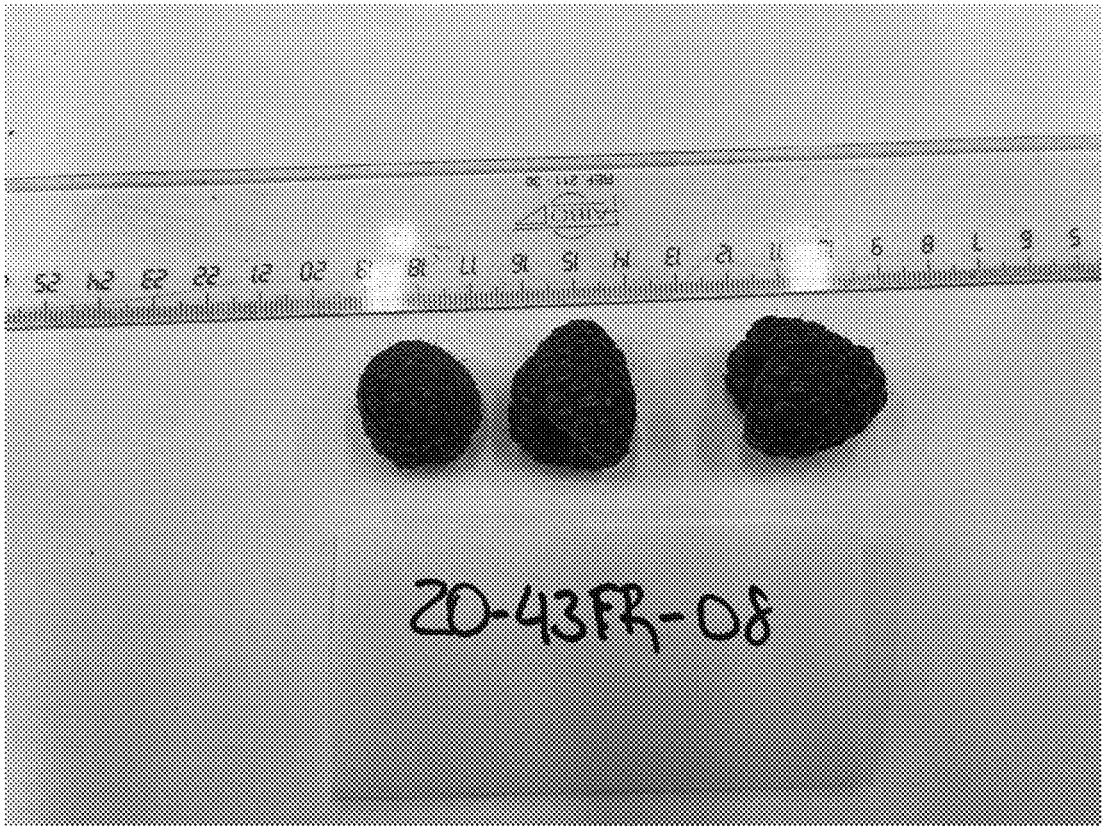
FIG. 3 shows the fruit of 'Aine'.

The following detailed descriptions set forth the distinctive characteristics of 'Aine'. The data which define these characteristics were collected from asexual reproductions carried out in Tariquejo, Villanueva de los Castillejos, Huelva, Spain. Data was collected in 2022-2023 on 6-month-old plants grown in a greenhouse in a hydroponic system. Color references are to The R.H.S. Colour Chart of The Royal Horticultural Society of London (R.H.S.), 6$^{th}$ edition (2015, reprint 2019).

Classification:
- *Family*.—Rosaceae.
- *Botanical*.—*Rubus idaeus* L.
- *Common*.—Raspberry.
- *Designation*.—'Aine'.

Parentage:
- *Female parent*.—'21-03FR-000' (not patented).
- *Male parent*.—Unknown.

Plant:
- *Height*.—210 cm.
- *Width*.—40 cm.
- *Length/width ratio*.—5.25.
- *Growth habit*.—Upright.
- *Hardiness zone*.—USDA Zone 10A.

Primocane (current year's cane):
- *Number*.—One.
- *Color*.—RHS 72A.
- *Cane length in autumn*.—210 cm.
- *Internodal distance at central ⅓ of cane*.—7.0 cm.
- *Time of cane emergence*.—April 15.

Previous year canes:
*Length of fruiting laterals.*—60 cm.
*Time of beginning flowering on previous year's cane.*—March 15.
*Time of beginning of fruit ripening on previous year's cane.*—April 15.
*Time of vegetative bud burst.*—January 15.
Very young shoot:
*Anthocyanin coloration of apex during rapid growth.*—RHS 143B.
Prickles (spines):
*Presence.*—Present.
*Length of the spines at 1 meter in height from the base of the plant.*—0.1 cm.
*Color.*—RHS N79B.
Leaves:
*Predominant number of leaflets.*—3.
*Profile of leaflets in cross section.*—Concave.
*Color of upper side.*—RHS 143B.
*Color of lower side.*—RHS N143D.
*Surface texture of upper side.*—Smooth.
*Surface texture of lower side.*—Rugose.
*Leaflet veination.*—Reticulate.
*Terminal leaflet.*—Average Length: 11.0 cm. Average Width: 7.0 cm. Length/width ratio: 1.57. Margin: Doubly serrate. Overall shape: Elliptic. Apex shape: Apiculate. Base shape: Cordate.
*Lateral leaflets.*—Average Length: 9.0 cm. Average Width: 6.0 cm. Length/width ratio: 1.5. Arrangement of lateral leaflets: Free. Margin: Doubly serrate. Overall shape: Elliptic. Apex shape: Apiculate. Base shape: Cordate.
*Rachis length between terminal leaflet and adjacent lateral leaflets.*—4.0 cm.
*Petiole.*—Length: 10.0 cm. Diameter: 0.3 cm. Color: RHS 72A.
Flowers:
*Diameter.*—2.3 cm.
*Petal.*—Length: 0.5 cm. Width: 0.3 cm. Length/width ratio: 1.6. Color of upper side: RHS 72D. Color of lower side: RHS 72D.
*Sepal.*—Length: 1.7 cm. Width: 0.5 cm. Shape: Lanceolate. Color: RHS 142D.
*Pedicel.*—Length: 2.3 cm. Diameter: 0.1 cm. Color: RHS 142D. Surface texture: Smooth.
*Peduncle.*—Color: RHS 142D. Intensity of anthocyanin coloration: Absent. Surface texture: Smooth.
Fruit:
*Length.*—3.5 cm.
*Diameter.*—3.2 cm.
*Length/width ratio.*—1.09.
*General shape in lateral view.*—Broad conical.
*Color.*—RHS N57B.
*Glossiness.*—Medium.
*Weight of single drupe.*—0.07 g.
*Number of drupelets per berry.*—77.
*Average weight per berry.*—6.3 g.
*Soluble solids (° brix).*—9.7.
Seed:
*Length.*—0.4 cm.
*Width.*—0.3 cm.
*Shape.*—Kidney.
*Color.*—RHS 153D.
Production:
*Main bearing type.*—Primocane.
*Primocane (current year's cane).*—Time of beginning of flowering: September 1. Time of beginning of fruit ripening: October 1. Length of fruiting period: 6 months. Yield: 24000 kg to 28000 kg per hectare per season from 5-month-old plants when grown in Huelva, Spain. Fruit storage life and shipping quality: 10 days. Market use: Fresh. Heat/cold tolerance: Heat tolerance between 7° C. and 40° C. Plant/fruit disease and pest resistance/susceptibility: None.

COMPARISON WITH PARENTAL LINE AND COMMERCIAL VARIETY

'Aine' can be compared to its female parent. Differences between the varieties are described in Table 1.

TABLE 1

Comparison with Female Parental Line

| Trait | Variety 'Aine' | Female parent '21-03FR-000' (not patented) |
|---|---|---|
| Fruit color | N57B | 63A |
| Precocity | October 1 | October 15 |
| Plant height | 210 cm | 250 cm |

'Aine' can be compared to the commercial Raspberry variety 'Diamond Jubilee' U.S. Plant Pat. No. 25,455). Differences between the varieties are described in Table 2.

TABLE 2

Comparison with Similar Variety

| Trait | Variety 'Aine' | Commercial line 'Diamond Jubilee' (U.S. Plant Pat. No. 25,455) |
|---|---|---|
| Fruit color | N57B | 44A |
| Internodal distance | 7 cm | 4.5 cm |
| Plant height | 210 cm | 156 cm |

We claim:

1. A new and distinct cultivar of raspberry plant named 'Aine' as shown and described herein.

* * * * *